(12) United States Patent
Lorence

(10) Patent No.: US 8,012,480 B2
(45) Date of Patent: Sep. 6, 2011

(54) DETECTION OF PROTEINS FROM CIRCULATING NEOPLASTIC CELLS

(75) Inventor: Robert M. Lorence, Bethesda, MD (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 171 days.

(21) Appl. No.: 12/297,420

(22) PCT Filed: Apr. 18, 2007

(86) PCT No.: PCT/US2007/066857
§ 371 (c)(1),
(2), (4) Date: Oct. 16, 2008

(87) PCT Pub. No.: WO2007/121465
PCT Pub. Date: Oct. 25, 2007

(65) Prior Publication Data
US 2009/0098138 A1    Apr. 16, 2009

Related U.S. Application Data

(60) Provisional application No. 60/745,016, filed on Apr. 18, 2006.

(51) Int. Cl.
*A61K 38/00* (2006.01)
*A61P 35/00* (2006.01)
*G01N 33/532* (2006.01)
*G01N 33/574* (2006.01)

(52) U.S. Cl. ............. 424/141.1; 435/7.23; 514/7.5; 514/19.2

(58) Field of Classification Search .................. None
See application file for complete search history.

(56) References Cited

U.S. PATENT DOCUMENTS

2008/0261243 A1   10/2008  Lorence et al.

FOREIGN PATENT DOCUMENTS

| WO | 00/47998 | | 8/2000 |
|---|---|---|---|
| WO | 03/065042 | A2 | 8/2003 |
| WO | 2004/008099 | A2 | 1/2004 |
| WO | WO2004/003554 | * | 1/2004 |
| WO | 2005/072507 | | 8/2005 |
| WO | 2006/031843 | | 3/2006 |
| WO | 2006/041959 | | 4/2006 |
| WO | WO2006/041959 | * | 4/2006 |

OTHER PUBLICATIONS

Harai et al (Endocrine Related Cancer, Dec. 2004, vol. 11, pp. 689-708).*
Sapin, et al., "Increased sensitivity of a new assay for anti-thyroglobulin antibody detection in patients with autoimmune thyroid diseases", Clinical Biochemistry, 3: 611-616, 2003.
Johnson, et al., Approval Summary of Erlotinib for Treatment of Patients with Locally Advanced or Metastatic Non-Small Cell Lung Cancer after Failure of at Least one Prior Chemotherapy Regimen, Clinical Cancer Research, 11(18): 6414-6417, 2005.
Vona, et al., "Isolation by Size of Epithelial Tumor Cells: A New Method for the Immunomorphological and Molecular Characterization of Circulating Tumor Cells", American Journal of Pathology, 156(1):57-63, Jan. 2000.
Lee, et al., "Development and Application of a Quantitative, Specific Assay for Cryptosporidium Parvum Oocyst Detection in High-Turbidity Environmental Water Samples", Am. J. Trop. Med. Hyg., 65(1): 1-9, 2001.
Liu, et al., "Rapid Detection of *Escherichia coli* O157:H7 Inoculated in Ground Beef, Chicken Carcass, and Lettuce Samples with an Immunomagnetic Chemiluminescence Fiber-Optic Biosensor", Journal of Food Protection, 66(3): 512-517, 2003.
Yu, et al., "Detection of biological threat agents by immunomagnetic microsphere-based solid phase fluorogenic- and electro-chemiluminescence", Biosensors & Bioelectronics, 14: 829-840, 2000.
Howanitz, "Immunoassay: Innovations in Label Technology", Arch. Pathol. Lab. Med., 112: 775-779, Aug. 1988.
Butcher, et al., "A sensitive time-resolved fluorescent immunoassay for metallothionein protein", Journal of Immunological Methods, 272:247-256, 2003.
Soukka, et al., "Supersensitive Time-resolved Immunofluorometric Assay of Free Prostate-specific Antigen with Nanoparticle Label Technology", Clinical Chemistry, 47(7): 1269-1278, 2001.
Zoon, et al., "Future Directions in Cancer Research: Impact of the Completion of the Human Genome", Toxicologic Pathology, 32(1):1-2, 2004.
MacGregor, et al., "Biomarkers of Cancer Risk and Therapeutic Benefit: New Technologies, New Opportunities, and Some Challenges", Toxicologic Pathology, 32(1):99-105, 2004.
Shirota, et al., "ERCC1 and Thymidylate Synthase mRNA Levels Predict Survival for Colorectal Cancer Patients Receiving Combination Oxaliplatin and Fluorouracil Chemotherapy", Journal of Clinical Oncology, 19(23):4298-4304, 2001.
Mann, et al., "Reliance on Hormone Receptor Assays of Surgical Specimens May Compromise Outcome in Patients With Breast Cancer", Journal of Clinical Oncology, 23(22):5148-5154, 2005.
Ciardiello, "Epidermal growth factor receptor inhibitors in cancer treatment", Future Oncol., 1(2), 221-234, 2005.
Macarulla, et al., "Epidermal Growth Factor Receptor (EGFE) Inhibitors in Gastrointestinal Cancer", Onkologie 29:99-105, 2006.
Cosaert, et al., "Platinum drugs in the treatment of non-small-cell lung cancer", British Journal of Cancer, 87: 825-833, 2002.
Desoize, et al., "Particular aspects of platinum compounds used at present in cancer treatment", Critical Reviews in Oncology/Hematology, 42: 317-325, 2002.

(Continued)

*Primary Examiner* — Karen Canella
(74) *Attorney, Agent, or Firm* — Lewis J. Kreisler

(57) ABSTRACT

The protein EGFR, ERCC1, RRM1, thymidylate synthase, or beta-tubulin from cancer cells is detected in a blood sample by enriching the cancer cells from the blood sample followed by performing on the enriched cancer cells an immunoassay capable of detecting the proteins mentioned above. Cancer patients overexpressing EGFR are treated with an anti-EGFR agent, for example cetuximab, panitumumab, erlotinib or gefitinib.

12 Claims, 2 Drawing Sheets

OTHER PUBLICATIONS

Abal, et al., "Taxanes: Microtubule and Centrosome Targets, and Cell Cycle Dependent Mechanisms of Action", Current Cancer Drug Targets, 3: 193-203, 2004.

Ferlini, et al., "Second Generation Taxanes: from the Natural Framework to the Challenge of Drug Resistance", Curr. Med. Chem.—Anti-Cancer Agents, 3: 133-138, 2003.

Chan, et al., "Pharmacokinetic Drug Interaction of Vinca Alkaloids: Summary of case Reports", Pharmacotherapy, 16 (6):1304-1307, 1998.

Agrawal, et al., "Tubulin Interacting Agents: Novel Taxanes and Epothilones", Current Oncology Reports, 5:89-98, 2003.

Farrell, "Preclinical Perspectives on the Use of Platinum Compounds in Cancer Chemotherapy", Seminars in Oncology, 31(6:14):1-9, 2004.

Carr, et al., "Genomic and proteomic approaches for studying human cancer: Prospects for true patient-tailored therapy", Human Genomics, 1(2):134-140, 2004.

Zhou, et al., Preclinical and Clinical Pharmacology of Vinca Alkaloids, Drugs, 44(4):1-16, 1992.

Lord, et al., "Low ERCC1 Expression Correlates with Prolonged Survival after Cisplatin plus Gemcitabine Chemotherapy in Non-Small Cell Lung Cancer" Clinical Cancer Research, 8:2286-2291, 2002.

Bergman, et al., "In vivo Induction of Resistance to Gemcitabine Results in Increased Expression of Ribonucleotide Reductase Subunit M1 as the Major Determinant", Cancer Research, 65(20):9510-9516, 2005.

Metzger, et al., "ERCC1 mRNA Levels Complement Thymidylate Synthase mRNA Levels in Predicting Response and Survival for Gastric Cancer Patients Receiving Combination Cisplatin and Fluorouracil Chemotherapy" Journal of Clinical Oncology, 16(1): 309-316, 1998.

Reed, "ERCC1 and Clinical Resistance to Platinum-Based Therapy", Clinical Cancer Research, 11(17): 6100-6102, 2005.

Farrugia, et al., "Thymidylate Synthase Expression in Advanced Colorectal Cancer Predicts for Response to Raltitrexed1", Clinical Cancer Research, 9: 792-801, 2003.

Mozzetti, et al., "Class III B-Tubulin Overexpression Is a Prominent Mechanism of Paclitaxel Resistance in Ovarian Cancer Patients", Clinical Cancer Research, 11: 298-305, 2005.

Seve, et al. "Expression of Class III B-Tubulin Is Predictive of Patient Outcome in Patients with Non-Small Cell Lung Cancer Receiving Vinorelbine-Based Chemotherapy", Clinical Cancer Research, 11(15): 5481-5486, 2005.

Henson, et al., "Back to the Drawing Board on Immunohistochemistry and Predictive Factors", Journal of the National Cancer Institute, 97(24): 1796-1797; 2005.

Pending (as of Oct. 8, 2008) claims from U.S. Appl. No. 12/296,476.

Pending (as of Oct. 8, 2008) claims from U.S. Appl. No. 12/296,458.

Kris, et al., "Efficacy of Gefitinib, an Inhibitor of the Epidermal Growth Factor Receptor Tyrosine Kinase, in Symptomatic Patients with Non-Small Cell lung Cancer: A Randomized Trial", Journal of American Medical Association, 290(16): 2149-2158, 2003.

Arends, et al., "Flexible dosing schedules for panitumumab (ABX-EGF) in cancer patients", Journal of Clinical Oncology, 23(16S): Abstract 3089, 2005.

Cunningham, et al., "Cetuximab Monotherapy and Cetuximab plus Irinotecan in Irinotecan-Refractory Metastatic Colorectal Cancer", The New England Journal of Medicine, 351(4): 337-345, 2004.

Hager, et al., "The use of a panel of monoclonal antibodies to enrich circulating breast cancer cells facilitates their detection", Gynecologic Oncology, 98(2): 211-216, 2005.

Richter, "Electrochemiluminescence (ECL)", Chemical Reviews, 104(6): 3003-3036, 2004.

Zieglschmid, et al., "Combination of Immunomagnetic Enrichment with Multiplex RT-PCR Analysis for the Detection of Disseminated Tumor Cells", Anticancer Research, 25(3A): 1803-1810, 2005.

Judson, et al., "Preoperative detection of peripherally circulating cancer cells and its prognostic significance in ovarian cancer", Gynecologic Oncology, 91(2): 389-394, 2003.

Smerage, et al., "The measurement and therapeutic implications of circulating tumour cells in breast cancer", British Journal of Cancer, 94(1): 8-12, 2006.

De Luca, et al., "Detection of Circulating Tumor Cells in Carcinoma Patients by a Novel Epidermal Growth Factor Receptor Reverse Transcription-PCR Assay", Clinical Cancer Research: 6(4): 1439-1444, 2000.

Zehentner, et al., "Mammaglobin as a Novel Breast Cancer Biomarker: Multigene Reverse Transcription-PCR Assay and Sandwich Elisa", Clinical Chemistry, 50(11): 2069-2076, 2004.

Ts'o, et al., "Detection of Intact Prostate Cancer Cells in the Blood of Men with Prostate Cancer", Urology, 49(6): 881-885, 1997.

Nicholson, et al., "EGFR and cancer prognosis", European Journal of Cancer, 37: S9-S15, 2001.

Griwatz, et al., "An immunological enrichment method for epithelial cells from peripheral blood", Journal of Immunological Methods, 183(2): 251-265, 1995.

Taback, et al., "Detection of Occult Metastatic Breast Cancer Cells in Blood by Multimolecular Marker Assay: Correlation with Clinical Stage o f Disease", Cancer Research, 61(24): 8845-8850, 2001.

Debad, et al., "Chapter 8: Clinical and Biological Applications of ECL", Electrogenerated Chemiluminescence, AJ Bard, Ed., pp. 359-396, 2004.

Yang, et al., "Electrochemiluminescence: A New Diagnostic and Research Tool", Bio/Technology, 12: 193-194, 1994.

Nakamura, et al., "Separation of breast cancer cell line from human blood using a quadrupole, magnetic flow sorter", Biotechnology Progress, 17(6):1145-1155, 2001.

* cited by examiner

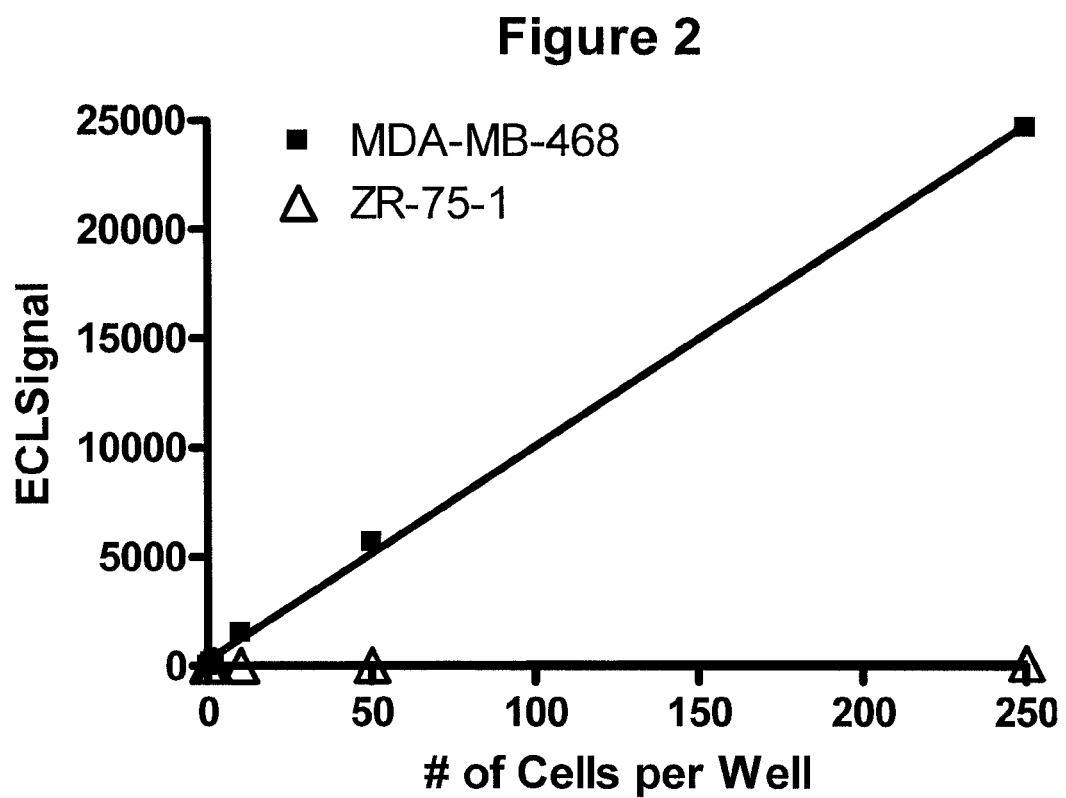

DETECTION OF PROTEINS FROM CIRCULATING NEOPLASTIC CELLS

BACKGROUND OF THE INVENTION

This invention addresses a significant and unmet medical need of providing for sensitive immunoassays which allow for advancement in the field of personalized cancer therapy. The general concept of personalized medicine for cancer has been the subject of recent reviews (Zoon K C, 2004, Toxicology Pathol. 32(Suppl 1):1-2; MacGregor J T, 2004, Toxicology Pathol. 32(Suppl 1):99-105; Carr K M et al., 2004 Hum Genomics 1:134-40). The approach of personalized medicine for cancer is to characterize the proteins or genes in the patient's tumor in order to determine the best course of therapy. For example, expression of certain genes or gene patterns at either the protein or mRNA level may predict either sensitivity or resistance to various classes of anticancer agents. Based on the expression in the patient's tumor, an agent may be selected for therapy or rejected for use in that particular patient. Table 1 lists some of the proteins whose overexpression is associated with either resistance or sensitivity of certain cancer agents.

TABLE 1

Proteins whose overexpression is associated with resistance or sensitivity of certain agents.

| Protein | Protein Class | Prediction of Resistance or Sensivitity of Various Agents |
| --- | --- | --- |
| EGFR | Membrane receptor with tyrosine kinase activity | Overexpression of EGFR predicts response to anti-EGFR agents such as cetuximab, panitumumab |
| ERCC1 | Enzyme (Member of Nucleotide Excision Repair Pathway) | Overexpression of ERCC1 predicts resistance to platinum agents (e.g., cisplatin, carboplatin, oxaliplatin) [Reed (2005; Clin Cancer Res 11: 6100-6102); Lord et al. (2002, Clin Cancer Res 8: 2286-91); Metzer et al., 1998, J Clin Oncol 16: 309-316; Shirota et al. (2001, J Clin Oncol 19: 4298-4304)] |
| Ribonucleotide reductase subunit M1 (RRM1) | Enzyme | Overexpression of RRM1 predicts resistance to gemcitabine [Bergman AM et al., 2005 Clin Cancer Res 65: 9510-6] |
| Thymidylate Synthase (TS) | Enzyme | Overexpression of TS predicts resistance to 5-FU; High TS expression predicts non-response to raltitrexed [Farrugia et al. (2003, Clin Cancer Res 9: 792-801)] |
| Beta-tubulin (class III) | Structural | Overexpression of beta-tubulin (class III) predicts resistance to taxanes [Mozzetti et al. (2005, Clin Caner Res 11: 298-305)]; Overexpression of beta-tubulin (class III) predicts resistance to vinca alkaloids [Seve et al., 2005, Clin Cancer Res 11: 5481-6] |

A major impediment for the advance in this field is the lack of a convenient, quick and objective assay to determine overexpression of such proteins. This invention addresses this issue.

One approach to assay expression of proteins in patient tumor tissue is to use immunohistochemical (IHC) staining of formalin fixed tumor tissue. But as pointed out by Mann et al. (2005, J Clin Oncol 22:5148-54), such an approach is time-consuming and often can give misleading results depending upon how the tissue was processed. Henson, D. E. (2005, J Natl Cancer Inst 97:1796-7) in his paper entitled: "Back to the Drawing Board on Immunhistochemistry and Predictive Markers", indicates that with so many variables (storage of the specimen, duration of fixation, type of fixative and conditions of tissue processing) and problems associated with each of them, it is difficult to properly control IHC testing and for all laboratories to "accept and sustain [these controls] seem impossible to realize."

SUMMARY OF THE INVENTION

This invention provides a method of assaying a protein from cancer cells in a blood sample comprising enriching the cancer cells from the blood sample followed by performing on the enriched cancer cells an immunoassay capable of detecting the protein from the enriched cancer cells. The immunoassay is capable of detecting the protein from one hundred cancer cells per milliliter of blood. Alternatively the immunoassay is capable of detecting one hundred sixty picograms of the protein. The protein is selected from the group consisting of epidermal growth factor receptor (including phosphorylated EGFR), excision repair cross-complementation group 1, ribonucleotide reductase subunit M1, thymidylate synthase, and beta-tubulin. The immunoassay generates a signal proportional to the number of molecules of the protein present in the cancer cells in the blood sample.

This invention provides a method of detecting the expression of a protein from cancer cells in a blood sample comprising isolating the cancer cells from the blood sample followed by making an extract from the isolated cancer cells followed by performing on the extract an immunoassay capable of detecting the protein, in which a positive immunoassay result indicates the presence of the protein in the cancer cells; wherein the protein is epidermal growth factor receptor; and the immunoassay is capable of detecting the protein from one hundred cancer cells per milliliter of blood. Alternatively the immunoassay is capable of detecting one hundred sixty picograms of the protein.

This invention provides a method of treating a cancer patient likely to benefit from treatment with anti-EGFR agent, comprising administering the anticancer agent to a patient identified as having overexpression of EGFR according to a method as described above.

The detection and assay methods described are convenient, quick and objective. Convenience: The approach outlined in this invention does not rely on the need for biopsy material. The patient's blood sample can be directly analyzed for the expression of the certain proteins in circulating tumor cells. Quick: Compared to IHC, the immunoassay of this invention avoids the need to retrieve blocks of tissue, de-paraffinize the blocks, cut slides and perform and interpret staining. Instead, a rapid immunoassay is used. Objective: Using the immunoassay of this invention, subjective scoring such as with IHC is avoided.

BRIEF DESCRIPTION OF THE FIGURES

FIG. 2. Further comparison of the ECL signal for the immunoassay detection of EGFR in lysates from MDA-MB-468 breast cancer cells (positive control for EGFR overexpression) versus ZR-75-1 (negative control for EGFR overexpression). Data from the same experiment as shown in FIG. 1 is used for this figure, except that data obtained from lysate material from 50 and 250 cells per well were also included in this graph in order to display an increased X-axis scale.

DETAILED DESCRIPTION OF THE INVENTION

Figure 1:
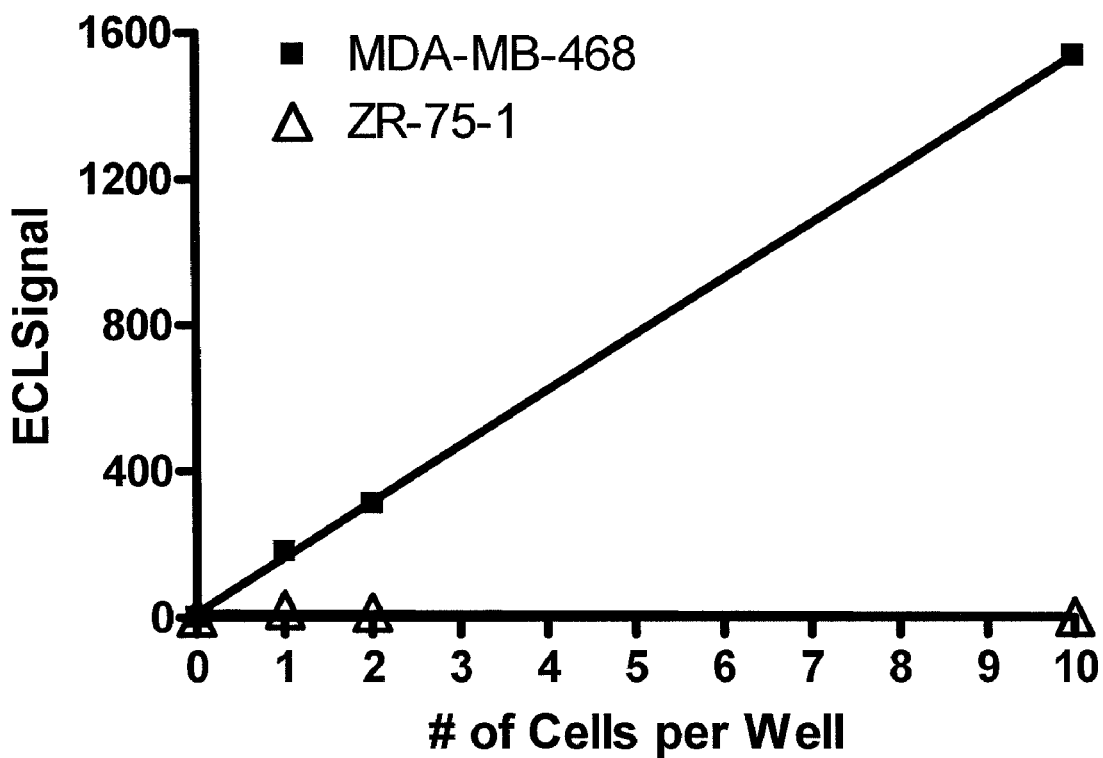
FIG. 1. Comparison of the ECL signal for the immunoassay detection of EGFR in lysates from MDA-MB-468 breast cancer cells (positive control for EGFR overexpression) versus ZR-75-1 (negative control for EGFR overexpression). Shown is the data using lysates from 1, 2, and 10 cells per well.

As used herein the transitional term "comprising" is open-ended. A claim utilizing this term can contain elements in addition to those recited in such claim. Thus, for example, the claims can read on methods that also include other steps not specifically recited therein, as long as the recited elements or their equivalent are present.

Abbreviations:
CTCs: circulating tumor cells
EGFR: epidermal growth factor receptor ERCC1: excision repair cross-complementation group 1
ECL: electrochemiluminescence
IHC: immunohistochemistry
PhosphoEGFR: phosphorylated EGFR
RRM1: ribonucleotide reductase subunit M1
TS: thymidylate synthase As used herein, the term "anti-EGFR agents" refers to anticancer agents that target EGFR, including antibodies and including small molecule inhibitors of the tyrosine kinase activity of EGFR (see Ciardiello F, 2005, Future Oncol 1:221-234; and Macarulla T et al., 2006, Onkologie 29:99-105) for reviews). Anti-EGFR agents include, but are not limited to: cetuximab, panitumumab, erlotinib, and gefitinib.

As used herein, the term "platinum agents" refers to compounds containing platinum with anticancer properties (see for recent reviews see Farrnell N P, 2004, Semin Oncol 31(6 Suppl 14):1-9; Cosaert J and Quoix E, 2002, Br J Cancer 87:825-33; Desoize B and Madoulet C, 2002, Crit Rev Oncol Hematol 42:317-25). Platinum agents include, but are not limited to: cisplatin, carboplatin, oxaliplatin, and nedaplatin.

As used herein, the term "taxanes", refers to paclitaxel and related compounds (see Abal M et al, 2004, Curr Cancer Drug Targets 3:193-203; Ferlini C et al., 2003, Curr Med Chem Anticancer Agents 3:133-8; and Agrawal N R et al., 2003, Curr Oncol Rep 5:89-98). Taxanes include, but are not limited to: paclitaxel and docetaxel.

As used herein, the term "vinca alkaloids", refers to vinorelbine and related compounds such as vinblastine and vincristine (for reviews, see Chan, 1998, Pharmacotherapy 18:1304-7; Zhou X.-J. and Rahmani R., 1992, Drugs, volume 44, supplement 4, pages 1-16).

This invention provides methods sensitive enough for quantifying the levels of proteins (consisting of EGFR, ERCC1, RRM1, TS and beta-tubulin) in circulating cancer cells in blood samples and provides methods for identifying those cancer patients who are likely to benefit from certain anticancer therapies (including, but not limited to: EGFR-targeted therapies; platinum agents; gemcitabine; 5-FU and raltirexed; taxanes; and vinca alkaloids). A convenient, highly sensitive and rapid means to test blood samples to identify additional patients who would benefit from such therapies would be an important advance in the cancer treatment field. As indicated below, a rapid and highly sensitive immunological assay to detect these cancer proteins in circulating cancer cells such as using electrochemiluminescence (ECL)-detection is a preferred means to accomplish this.

This invention is based on combining the high specificity of procedures used to isolate circulating cancer cells from blood with the high sensitivity of certain immunologically based assays such as ECL. Circulating cancer cells are first enriched. The term "enriching the cancer cells" refers to the implementation of any processing step that increases the ratio of cancer cells relative to non-cancer cells. One preferred method of enrichment uses immunomagnetic beads by isolating and purifying the circulating cancer cells from blood. Another preferred method of enrichment consist of the collection of a whole blood sample in a Becton Dickinson BD VACUTAINER CPT tube and the obtaining by centrifugation (as per Becton Dickinson recommended procedures) of a peripheral blood mononuclear fraction that contains enriched cancer cells. Another preferred method of enrichment of cancer cells consist of collection of a whole blood sample followed by the lysis of red blood cells.

In an embodiment of the detection method of this invention the sensitivity level of the immunological assay is such that the assay is capable of detecting proteins from cancer cells when spiked into blood at a concentration of less than or equal to 100 cells per milliliter of blood, more preferably less than or equal to 30 cells per milliliter of blood, more preferably less than or equal to 10 cells per milliliter of blood, more preferably less than or equal to 3 cells per milliliter of blood, and most preferably less than or equal to 1 cell per milliliter of blood. In an embodiment of the invention in which sensitivity is defined in terms of the amount of protein that can be detected, the assay can detect sixty-four picograms of the protein, more preferably sixteen picograms of the protein, more preferably four picograms of the protein, still more preferably one picogram of the protein.

A sample (usually in the range of approximately 8 to 20 ml) of blood from a patient with cancer, especially breast cancer, is taken. Steps include as detailed below:
 1. Removal of red blood cells
 2. Optional negative selection to further deplete normal leukocytes. A preferred embodiment includes this step.
 3. Positive selection for circulating tumor cells (CTCs)
 4. Extraction of tumor cell proteins
 5. Quantification of tumor cell proteins on CTCs 1. Removal of Red Blood Cells.

A variety of methods are available to remove red cells including but not limited to separation based on density (such as collection of blood directly into the Becton Dickinson BD VACUTAINER CPT tubes) followed by centrifugation) and commercial lysing buffers such as PURESCRIPT RBC lysis buffer (Gentra, Minneapolis), FACS lysing solution (BDIS), IMMUNOLYSE (Coulter), OPTILYSE B (Immunotech), and ACK lysing buffer (Biosource, Rockville, Md.).

A preferred method uses the BD Vacutainer CPT tubes with anticoagulant (EDTA or citrate). These tubes contains a material that upon correct centrifugation (1,100×g for 10 minutes, swing-out bucket rotor) allows for elimination of red blood cells and neutrophils. After centrifugation, the bottom of the tube contains a cell pellet of erythrocytes (red blood cells) and neutrophils. Above the cell pellet is a gel barrier and above the gel barrier are tumor cells, lymphocytes and monocytes as a band at the bottom of the plasma. The tumor cells, lymphocytes and monocytes can then be readily collected from the top above the gel barrier. This method is preferred as it removes not only the red blood cells but also the neutrophils.

2. Negative Selection to Further Deplete Normal Leukocytes.

A preferred embodiment of this invention uses negative selection step for isolation of tumor cells. Negative selection allows for further depletion of leukocytes especially the lymphocytes and monocytes. This step comprises the use of antibodies that are bispecific for both leukocyte antigens, especially CD45, the common leukocyte antigen, and for a red blood cell antigen such as glycophorin A. A commercially available cocktail of such bispecific antibodies is available from STEMCELL TECHNOLOGIES (Rosettesep Catalog #15127 and #15167). This cocktail includes bispecific antibodies against glycophorin A and against a variety of cell surface antigens on human hematopoietic cells (CD2, CD16, CD19, CD36, CD38, CD45, CD66b). One or more of these bispecific antibodies are added to the BD Vacutainer CPT tubes before blood collection. In a preferred embodiment, the cocktail of bispecific antibodies against more than one leukocyte-associated CD molecule is used. When the blood is introduced into the CPT vacutainer tube, the bispecific antibodies form immunorosettes each consisting of leukocytes plus many red blood cells. These immunorosettes have a density approximately that of red blood cells and when centrifuged are found in the red blood cell pellet, thus further removing leukocytes from the tumor cell fraction found above the cell pellet and gel barrier. The fraction with the tumor cells in plasma is collected for further processing.

3. Positive Selection for Circulating Tumor Cells (CTCs)

A preferred method of isolating CTCs uses immunomagnetic beads. Other methods of isolation of circulating cancer cells include filtration (Vona G et al., 2000, Am J Pathol. 2000 156:57-63). In a preferred embodiment, the immunomagnetic beads have antibodies against antigens found selectively on the surface of cancer cells such as epithelial cell adhesion molecule (EpCAM), cytokeratins such as cytokeratin-19 and especially a cocktail of antibodies against cytokeratins and other surface markers, carcinoembryonic antigen (CEA), bladder tumor antigen, CA19.9, CA125, CD138 (Syndecan-1), CD227 (MUC1), E-Cadherin, P-Cadherin, EGFR, Her2/neu, AUA1, TACSTD1, and Galectin-3; and (b) in the case of leukemia or lymphoma cells: CD3, CD19, CD20, CD34, CD38, CD45, CD123, CD138, B220, HLA-DR and CXCR4; c) in the case of cancer stem cells: CD34, CD40, CD48, CD49f, CD90, CD96, CD123, CD133, CD150, CD244, CXCR4, ABCG2 and ESA. The immunomagnetic beads may be of various sizes (50 microns to less than 200 nm) and include DYNAL beads (>1.5 microns to about 50 microns) with antibodies against EpCAM (which are commercially available). In an embodiment of the invention, EasySep™ human EpCAM positive selection cocktail and EasySep™ Magnetic nanoparticles (Stemcell Technologies) are added to the fraction with the tumor cells in plasma from the previous step. A magnet is then used to separate tumor cells from the rest of the material and the tumor cells are washed with an aqueous solution.

4. Extraction of Tumor Cell Proteins

In the next step, enriched or purified tumor cells are then ready for cell lysis and extraction of CTC proteins. A variety of commercially available kits are used such as, but not limited to:

Pierce Lysis Buffer [M-PER® Extraction Reagent (Product number 78501 from Pierce Biotechnology, Inc., Rockford, Ill.)] and Sigma Lysis Buffer [Sigma CelLytic™-M (Sigma Product Number C 2978, Sigma-Aldrich, Inc., St. Louis, Mo. 63103)].

After lysis, cell debris is removed by centrifugation leaving the lysate supernatant with the antigens to be measured.

In a preferred embodiment, the Sigma or the Pierce kit is used.

5. Quantification of Tumor Cell Proteins on CTCs

Detection and quantification are then accomplished by use of a highly sensitive sandwich immunoassay using antibodies which bind to the protein being assayed. Table 1 lists the proteins that can be assayed in this invention. A variety of antibodies can be used for the immunoassay, preferably using at least one polyclonal antibody and most preferably, using two polyclonal antibodies.

Detection of each protein is accomplished by using a sandwich immunoassay with the two sets of antibodies directed against the protein being analyzed. In a preferred embodiment using electrochemiluminescence, one antibody is linked to biotin and the other linked to a ruthenium detecting molecule.

In a preferred embodiment of the invention, an antibody against the protein is linked with biotin and the second antibody against the protein is labeled with a detecting molecule. In the case of electrochemiluminescence (ECL), the detecting molecule is ruthenium. There is abundant literature in the public domain provides amply useful methods for linking ruthenium to antibodies (e.g., Lee et al., Am J Trop Med Hyg 2001, 65:1-9). The cell lysate supernatant is mixed with the two antibodies and incubated briefly followed by the addition of streptavidin-coated magnetic beads in a solution containing tripropylamine. With application of an electric potential and in the presence of the target antigen, the ruthenium label is excited and light is emitted and detected using an ECL detecting instrument (such as the ORIGEN analyzer or a commercially available instrument like the M-Series® 384 from BioVeris Corporation, Gaithersburg, Md. or Elecsys® 1010 or Elecsys® 2010 from Roche Diagnostics, Indianapolis, Ind.)

In a preferred embodiment of the invention, the immunoassay utilized in accordance with this invention can use one of the following combinations of antibodies (see Table 2 for examples of antibodies against specific proteins):
 1. Two sets of polyclonal antibodies against the protein (the most preferred embodiment)
 2. A polyclonal antibody and a monoclonal antibody against the protein.
 3. Two monoclonal antibodies against the protein.

TABLE 2

Examples of antibodies.

| Protein | Antibodies |
|---|---|
| EGFR | Rabbit polyclonal antibody (AF231; R&D Systems, Inc., Minneapolis, MN); Monoclonal antibody (MAB1095, R&D Systems); Also antibodies against phosphoEGFR such as R&D catalog numbers AF1095 polyclonal with specificity towards EGFR with phosphorylation of amino acid Y1173; MAB1095 monoclonal with specificity towards EGFR with phosphorylation of amino acid Y1068; and AF3394 polyclonal with specificity towards EGFR with phosphorylation of amino acid Y845. |
| ERCC1 | Monoclonal antibody 8F1 (ab2356, Novus Biologicals, Littleton CO); Monoclonal antibody Catalog Number ERCC11-M (Alpha Diagnostics, San Antonio, TX) |
| RRM1 | Polyclonal antibody (Catalog Number H00006240-A01, Abnova Corporation, Taipei, Taiwan); Monoclonal antibody (Catalog Number MAB3033, Chemicon International, Inc., Temecula, CA) |
| TS | Rabbit polyclonal antibody (Catalog Number ab22254, Novus Biologicals); Mouse monoclonal antibody TS106 (Catalog Number NB 600-550, Novus Biologicals); Mouse monoclonal antibody 3A7.A11 (Catalog Number ab990, Novus Biologicals); Sheep polyclonal antibody (Catalog Number ab7398, Novus Biologicals) |
| Beta-tubulin | Polyclonal and monoclonal antibodies against Class III beta tubulin: See Seve et al., 2005, Clin Cancer Res 11: 5481-6 and see Mozzetti et al., 2005, Clin Cancer Res 11: 298-305 for examples of antibodies against Class III beta tubulin. |

The immunoassay of this invention is capable of detecting protein expression from 100 or less cancer cells added per ml of blood from a human volunteer without cancer, and preferably 30 or less cells per ml of blood.

Besides electrochemiluminescence, other immunoassays that can yield a high sensitivity required for this application include, but are not limited to:

a) Chemiluminescence such as described by Liu Y et al., 2003 (J Food Protection 66:512-7).

b) Fluorogenic-chemiluminescence (FCL) as described by Yu H et al., 2000 (Biosens Bioelectron 14:829-40)

c) Fluoresence polarization immunoassay (see Howanitz J H, 1988 Arch Pathol Lab Med 112:775-9)

d) Time-resolved fluorescence immunoassay (Butcher H et al., 2003, J Immunol Methods 272:247-56; Soukka et al., 2001, Clin Chem 47:1269-78; Howanitz J H, 1988 Arch Pathol Lab Med 112:775-9)

In a preferred embodiment, the relative quantity of circulating tumor cells used in the assay is estimated. This allows for a ratio of total protein per cell to be obtained and can be compared to control standards of cancer cells with high, moderate, and low levels of protein per cell. This is a preferred embodiment since it eliminates a false positive situation in which there are many CTCs having a low level of protein expression that may give a signal that mimics that obtained from a small number of CTCs with a high level of expression. In this embodiment, a variety of approaches can be used to estimate relative cell numbers including flow cytometric analysis, quantification of total DNA or DNA related antigens such as histones from lysed cells (there is 6 pg DNA per diploid cell), quantification of a house-keeping gene product like beta-actin, and turbidity or absorbance measurements.

Due to its sensitivity the method according to this invention is useful for identifying cancer patients likely to benefit from or not benefit from specific anticancer treatments.

The invention will be better understood by reference to the following examples, which illustrate but do not limit the invention described herein.

EXAMPLES

Example 1

A patient with cancer comes into the office and a blood sample is collected in a tube to prevent clotting. Cancer cells are isolated and proteins extracted using a commercially available kit such as Pierce Lysis Buffer and Sigma Lysis Buffer. A ruthenium-labeled rabbit polyclonal antibody against EGFR and a biotinylated polyclonal antibody (also against EGFR) is added and the followed by the addition of a suspension of magnetic beads with avidin attached and then a solution containing tripropylamine. An electric current is applied and electrochemiluminescence (ECL) is detected using an ECL detection device such as one commercially available (BioVeris Corporation or Roche Diagnostics). The signal is proportional to the amount of EGFR found in the circulating tumor cells.

Example 2

Methods are as in example 1, except the antibodies are against ERCC1.

Example 3

Methods are as in example 1, except the antibodies are against RRM1

Example 4

Methods are as in example 1, except the antibodies are against TS.

Example 5

Methods are as in example 1, except the antibodies are against beta-tubulin

Example 6

In this example, the sensitivity of detecting EGFR from cancer cells using a sandwich immunoassay using electrochemiluminescence is examined.

A PBS assay buffer is prepared:

Assay Buffer 0.5% Tween-20 and 0.5% bovine serum albumin (BSA) in PBS (phosphate buffered saline)

Anti-EGFR polyclonal antibody is first obtained in both biotinylated (BAF231 from R&D Systems) and non-biotinylated forms (AF231 from R&D systems). The non-biotinylated polyclonal antibody is ruthenium labeled ("TAG-labeled") as follows:

1.5 µg/µl ruthenium label (BV-TAG-NHS Ester, Catalog # 110034; BioVeris Corporation, Gaithersburg, Md., USA) is prepared in DMSO.

For 500 µl of antibody, 18.8 µl BV-TAG-NHS is added and for 200 µl of polyclonal antibody, 3.8 µl BV-TAG-NHS is added. In each case, the solution is incubated for one hour and the reaction stopped by the addition of 20 µl of 2M glycine.

Uncoupled BV-TAG-NHS Ester in each reaction mixture is removed using a PD-10 gel filtration column, pre-equilibrated with PBS (including 0.08% sodium azide), which is also used for elution. For each labeled antibody, the protein concentration in each fraction is determined by protein assay and the fractions with high protein content is used in subsequent examples.

The ruthenium-labeled polyclonal antibody and the biotinylated polyclonal antibody are referred hereafter in this example as "TAG-pAb" and "Biotin-pAb".

A431 carcinoma cancer cells (from ATCC, Manassas, Va.) are grown in 6-well tissue culture plates as per ATCC recommended conditions, washed two times with PBS, and an aliquot counted using a hemacytometer. These cells are lysed using Sigma Lysis Buffer [Sigma CelLytic™-M (Sigma Product Number C 2978, Sigma-Aldrich, Inc., St. Louis, Mo. 63103)]. Cell lysis is performed as per the manufacture's recommendation with the addition of 5 minutes of vigorous vortexing prior to cell debris removal. Cell debris is removed from the cell lysate by centrifugation at 14,000 rpm for 30 minutes in an Eppendorf Centrifuge (Model 5415C).

An electrochemiluminsence assay is performed as follows:
Sequentially, to each well, cell lysate supernatants are added (the amount of lysate per well is varied from that extracted from 3 to 100 cells; control wells without extract are also used) and then 50 µl/well of a mixture of TAG-Ab and Biotin-Ab (e.g., at a concentration between 0.5 to 2 µg/ml each; diluted into the the PBS assay buffer) are added to wells of a 96-well U-bottom polypropylene plate and are incubated at room temperature with constant shaking (e.g., for 2 hours).
10 µg of magnetic streptavidin beads (e.g., DYNABEADS M-280 Streptavidin, Catalog #110028, BioVeris Corporation, Gaithersburg, Md.) in 25 µl is added to each well and incubated with constant shaking (e.g., for 30 minutes).
PBS assay buffer is added to each well to make a final volume of 250 µl per well. All conditions are tested in at least duplicate wells. The 96 well plate is then analyzed for electrochemiluminescence using the M8 M-Series® Analyzer (Catalog Number 310800, BioVeris Corporation, Gaithersburg, Md.).

Using this immunoassay, EGFR from at least ten A431 carcinoma cells are detectable with a signal above background.

Example 7

In this example, the sensitivity of detecting recombinant EGFR using a sandwich immunoassay using electrochemiluminescence was examined.

A PBS assay buffer was prepared:
Assay Buffer: 0.5% Tween-20 and 0.5% bovine serum albumin (BSA) in PBS (phosphate buffered saline, pH 7.2)
A standard diluent was prepared:
Standard Diluent: 1% bovine serum albumin (BSA) in PBS (phosphate buffered saline, pH 7.2)

Anti-EGFR polyclonal antibody was first obtained in both biotinylated (BAF231 from R&D Systems) and non-biotinylated forms (AF231 from R&D systems). The non-biotinylated polyclonal antibody is ruthenium labeled ("TAG-labeled") according the methods of Lorence & Lu (WO 2006/041959 A2).

The ruthenium-labeled polyclonal antibody and the biotinylated polyclonal antibody are referred hereafter in this example as "TAG-pAb" and "Biotin-pAb".

Recombinant EGFR protein was obtained in the form of EGFR-Fc protein (a chimeric protein consisting of the extracellular domain fused to the Fc region of human IgG via a linker group; R&D systems, catalog #344-ER).

An electrochemiluminescence assay was performed as follows:
Standards were diluted in 1 ml PBS (pH 7.2 with 0.35% BSA and 0.05% sodium azide) to form a stock solution of 50 µg/mL.
Standards were diluted in Standard Diluent to yield 1600, 160, 16, and 4 pg/well when 25 µL was used per well. To each well of a 96-well U-bottom polypropylene plate (with 25 µL of standard per well) were added 50 µl/well of a mixture of TAG-Ab and Biotin-Ab (e.g., at a concentration of 1.0 µg/ml in the 50 µl prior to addition) and the resultant solution was incubated at room temperature with constant shaking (for 2 hours).
10 µg of magnetic streptavidin beads (e.g., DYNABEADS M-280 Streptavidin, Catalog #110028, BioVeris Corporation, Gaithersburg, Md.) in 25 µl was added to each well and incubated with constant shaking (for 30 minutes).
PBS Assay Buffer was added to each well to make a final volume of 250 µl per well. All conditions were tested in at least duplicate wells. The 96 well plate was then analyzed for electrochemiluminescence using the M-Series® 384 Analyzer (BioVeris Corporation, Gaithersburg, Md.).

Using this immunoassay, as little as 4 pg per well of EGFR standard was detectable with a signal above background (Table 3).

TABLE 3

Electrochemiluminescence (ECL) detection of recombinant EGFR by immunoassay using ruthenium-labeled polyclonal (TAG-pAb) and biotinylated polyclonal antibody (Biotin-pAb).

| EGFR (pg/well) | Mean ECL Signal (above background)* |
|---|---|
| 4 | 443 |
| 16 | 1187 |
| 160 | 8107 |
| 1600 | 69113 |

*Mean ECL signal above the mean signal from control wells with no antigen.

Example 8

In this example, the specificity for an ECL immunoassay against EGFR for detecting EGFR from overexpressing vs. non-overexpressing cancer cells was determined along with a repeat determination of the sensitivity of detecting recombinant EGFR. Methods were as that used in Example 7 with the additional analysis of cell extracts from MDA-MB-468 breast carcinoma cells (positive control cells for EGFR overexpression) and ZR-75-1 breast carcinoma cells (negative for EGFR overexpression) were analyzed.

MDA-MB-468 and ZR-75-1 cells (from ATCC, Manassas, Va.) were grown in 6-well tissue culture plates as per ATCC recommended conditions, washed two times with PBS, and an aliquot counted using a hemacytometer. Lysis of SK-BR-3 cells and obtaining the supernatant was performed using the Pierce Lysis Buffer [catalog #78501; Pierce Biotechnology, Rockford, Ill.] with Pierce protease inhibitor [catalog #78410; Pierce Biotechnology]. The amount of lysate supernatant per well was varied from that extracted from 1 to 250 MDA-MB-468 or ZR-75-1 cells and analyzed for EGFR using the immunoassay described in Example 7.

Using the EGFR standard, as little as 4 pg per well of EGFR standard was again detectable with a signal above background (Table 4).

TABLE 4

Electrochemiluminescence (ECL) detection of recombinant EGFR by immunoassay using ruthenium-labeled polyclonal (TAG-pAb) and biotinylated polyclonal antibody (Biotin-pAb).

| EGFR (pg/well) | Mean ECL Signal (above background)* |
|---|---|
| 4 | 627 |
| 16 | 1919 |
| 160 | 12961 |
| 1600 | 113532 |

*Mean ECL signal above the mean signal from control wells with no antigen.

The results from this experiment using cell lysates are presented in FIGS. 1 and 2. FIG. 1 graphically displays the lower end of the data set to best see the ability of this assay to detect EGFR from low cell numbers. FIG. 1 only includes data for the cell range up to 10 cells per well. FIG. 2 graphically displays the entire data set (up to 250 cells per well).

EGFR was detectable and above baseline from lysates from MDA-MB-468 cells in this experiment including those wells using the lowest amount of MDA-MB-468 lysate in this experiment (lysate from 1 cell added per well; FIG. 1). Furthermore, the lysate from the MDAMB-468 cells (positive control for EGFR overexpression) gave a much higher signal in the immunoassay for EGFR than the lysate from ZR-75-1 cells (negative for EGFR overexpression) over the entire tested range from 1 to 250 cells per well, indicating the high specificity of the results for EGFR detection (FIGS. 1 & 2).

What is claimed is:

1. A method of assaying a protein from cancer cells in a blood sample comprising enriching the cancer cells from the blood sample followed by lysing the enriched cells and performing on the lysed cancer cells an immunoassay capable of detecting the protein from the cancer cells; wherein
    the immunoassay uses electrochemiluminescence for detection
    the immunoassay has a sensitivity defined by being capable of quantifiably detecting the protein from thirty cancer cells per milliliter of blood or by being capable of detecting sixty-four picograms of the protein; and
    the protein is selected from the group consisting of epidermal growth factor receptor, excision repair cross-complementation group 1, ribonucleotide reductase subunit M1, thymidylate synthase, and beta-tubulin; and
    the immunoassay generates a signal proportional to the number of molecules of the protein present in the cancer cells in the blood sample.

2. A method of detecting the expression of a protein from cancer cells in a blood sample comprising isolating the cancer cells from the blood sample followed by making an extract from the isolated cancer cells followed by performing on the extract an immunoassay capable of detecting the protein, in which a positive immunoassay result indicates the presence of the protein in the cancer cells;
    wherein
        the immunoassay uses electrochemiluminescence for detection
        the protein is epidermal growth factor receptor; and
        the immunoassay has a sensitivity defined by being capable of detecting the protein from thirty cancer cells per milliliter of blood or by being capable of detecting sixty-four picograms of the protein.

3. The method of claim 1, wherein the immunoassay is capable of detecting the protein from ten cancer cells per milliliter of blood.

4. The method of claim 3, wherein the immunoassay is capable of detecting the protein from three cancer cells per milliliter of blood.

5. The method of claim 1, wherein the immunoassay is capable of detecting four picograms of the protein.

6. A method of treating a cancer patient likely to benefit from treatment with an anti-EGFR agent, comprising administering the agent to the patient whose blood sample tested positive for epidermal growth factor receptor in the method of claim 1.

7. The method of claim 6 wherein the agent is selected from the group consisting of cetuximab, panitumumab, erlotinib, and gefitinib.

8. The method of claim 2, wherein the immunoassay is capable of detecting the protein from ten cancer cells per milliliter of blood.

9. The method of claim 8, wherein the immunoassay is capable of detecting the protein from three cancer cells per milliliter of blood.

10. The method of claim 2, wherein the immunoassay is capable of detecting four picograms of the protein.

11. A method of treating a cancer patient likely to benefit from treatment with an anti-EGFR agent, comprising administering the agent to the patient whose blood sample tested positive in the method of claim 2.

12. The method of claim 11 wherein the agent is selected from the group consisting of cetuximab, panitumumab, erlotinib, and gefitinib.

* * * * *

UNITED STATES PATENT AND TRADEMARK OFFICE
CERTIFICATE OF CORRECTION

| | | |
|---|---|---|
| PATENT NO. | : 8,012,480 B2 | Page 1 of 1 |
| APPLICATION NO. | : 12/297420 | |
| DATED | : September 6, 2011 | |
| INVENTOR(S) | : Robert M. Lorence | |

It is certified that error appears in the above-identified patent and that said Letters Patent is hereby corrected as shown below:

Column 10, line 56, delete "SK-BR-3".

Signed and Sealed this
Eighteenth Day of October, 2011

David J. Kappos
*Director of the United States Patent and Trademark Office*